(12) United States Patent
Broshears

(10) Patent No.: US 7,416,532 B1
(45) Date of Patent: Aug. 26, 2008

(54) TRACH SENSORY ALERT SYSTEM

(75) Inventor: Loretta S. Broshears, Spring Hill, FL (US)

(73) Assignee: Loretta Broshears Doughty, Tallahassee, FL (US)

( * ) Notice: Subject to any disclaimer, the term of this patent is extended or adjusted under 35 U.S.C. 154(b) by 1153 days.

(21) Appl. No.: 10/035,472

(22) Filed: Oct. 23, 2001

Related U.S. Application Data

(60) Provisional application No. 60/242,993, filed on Oct. 23, 2000.

(51) Int. Cl.
*A61B 5/00* (2006.01)

(52) U.S. Cl. .................................................... 600/549

(58) Field of Classification Search ................ 600/537, 600/529, 549; 340/608; 712/131; 128/207.14
See application file for complete search history.

(56) References Cited

U.S. PATENT DOCUMENTS

| 3,903,876 | A | * | 9/1975 | Harris | 600/537 |
| 4,046,139 | A | * | 9/1977 | Horn | 600/549 |
| 4,830,022 | A | * | 5/1989 | Harshe et al. | 600/537 |
| 5,070,321 | A | * | 12/1991 | Einhorn et al. | 600/537 |

* cited by examiner

*Primary Examiner*—Max Hindenburg
*Assistant Examiner*—Jonathan M Foreman

(57) ABSTRACT

An alarm device that includes a temperature sensor placed in the tube of a trach tube and which is adapted to activate an audible alarm when predetermine low temperature has been detected.

1 Claim, 1 Drawing Sheet

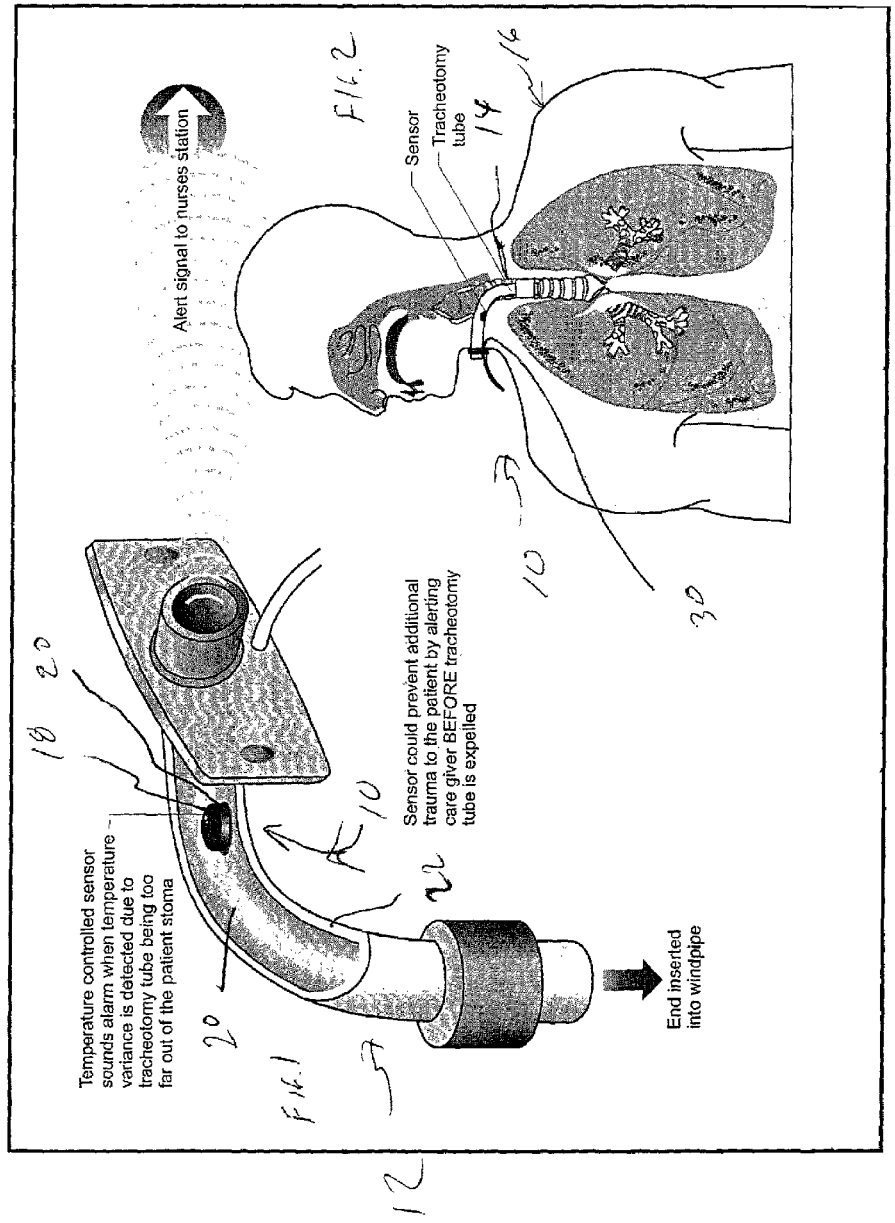

TRACH SENSORY ALERT SYSTEM

This application claims the benefit of priority to U.S. Provisional Application No. 60/242,993 filed Oct. 23, 2000.

TECHNICAL FIELD

The present invention relates to medical safety equipment and more particularly to a trach tube sensory alert mechanism that includes an alarm system with temperature controlled sensor which is positioned within the tracheotomy tube of a patient that is inserted into the windpipe area and which is configured to emit an audible alert alarm when the temperature detected by the sensor falls below a predetermined set temperature to alert the patient care givers that the trach tube may have been pulled out or a drastic drop in body temperature has occurred.

BACKGROUND OF INVENTION

The disconnection of tracheotomy tubes can cause death through asphyxiation if the trach opening is closed or cannot be reopened because a tracheotomy tube has been fully pulled out. It would be desirable, therefore, to have an alert device which would sense the temperature of the interior or exterior of the trach tube and which would provide an audible alarm for alerting care givers that the trach tube is working its way out of the trach opening and/or the body temperature of the patient has fallen below a safe level.

SUMMARY OF INVENTION

It is thus an object of the invention to provide a trach sensory alert system that includes an alarm system with temperature controlled sensor which is positioned within the tracheotomy tube of a patient that is inserted into the windpipe area and which is configured to emit an audible alert alarm when the temperature detected by the sensor falls below a predetermined set temperature to alert the patient care givers that the trach tube may have been pulled out or a drastic drop in body temperature has occurred.

Accordingly, a trach sensory alert system is provided. The trach sensory alert system includes an alarm system with temperature controlled sensor which is positioned within the tracheotomy tube of a patient that is inserted into the windpipe area and which is configured to emit an audible alert alarm when the temperature detected by the sensor falls below a predetermined set temperature to alert the patient care givers that the trach tube may have been pulled out or a drastic drop in body temperature has occurred.

BRIEF DESCRIPTION OF DRAWINGS

For a further understanding of the nature and objects of the present invention, reference should be had to the following detailed description, taken in conjunction with the accompanying drawings, in which like elements are given the same or analogous reference numbers and wherein:

FIG. 1 shows an exemplary embodiment of a trach tube with the trach sensory alert positioned within the stoma tube.

FIG. 2 shows the stoma tube into the patient and the sensor positioned within the neck area of the patient.

EXEMPLARY EMBODIMENTS

FIGS. 1 and 2 show various aspects of an exemplary embodiment of the trach sensory alert system of the present invention generally designated 10 in use with a representative tracheotomy device 12 and installed in the trachea 14 of a representative patient 16. Trach sensory alert system 10 includes a temperature controlled sensor 18 that is placed within the alarm portion 20 of a trach tube 22 of tracheotomy device 12. In use, trach tube 22 is positioned within the trachea 14 of patient 16 and is therefore subjected to the normal body temperature of patient 16. Should tracheotomy device 12 begin to work its way out through the ostomy opening 30 through which it is inserted, sensor 18 will detect a corresponding drop in body temperature and trigger an alerting device 20 contained within itself which generates a high pitched audible alarm to alert the patient 16 as well as any care givers.

It can be seen from the preceding description that a trach sensory alert system has been provided.

It is noted that the embodiment of the a trach sensory alert system described herein in detail for exemplary purposes is of course subject to many different variations in structure, design, application and methodology. Because many varying and different embodiments may be made within the scope of the inventive concept(s) herein taught, and because many modifications may be made in the embodiment herein detailed in accordance with the descriptive requirements of the law, it is to be understood that the details herein are to be interpreted as illustrative and not in a limiting sense.

What is claimed is:

1. A method of alerting a care giver before a tracheotomy tube is expelled comprising:
   providing a tracheotomy tube;
   positioning within the interior lumen of said tracheotomy tube an alert system, wherein the alert system includes a temperature controlled sensor for sensing the temperature of the interior or exterior of said tracheotomy tube and an alerting device for providing an audible alarm;
   inserting the tracheotomy tube within a patient's trachea;
   subjecting said temperature controlled sensor to the normal body temperature of the patient;
   detecting a corresponding drop in body temperature due to said tracheotomy tube being too far out of the patient's stoma;
   triggering said alerting device and generating a high pitched audible alarm.

* * * * *